United States Patent [19]

Szelke et al.

[11] 4,424,207

[45] Jan. 3, 1984

[54] ENZYME INHIBITORS

[75] Inventors: Michael Szelke, Ruislip; David M. Jones, Hayes; Allan Hallett, Wembley, all of England

[73] Assignee: Ferring Pharmaceuticals Limited, Feltham, England

[21] Appl. No.: 290,620

[22] Filed: Aug. 5, 1981

[51] Int. Cl.³ .................... C07C 103/52; A61K 37/02
[52] U.S. Cl. ............................. 424/177; 260/112.5 R; 260/112.5 E
[58] Field of Search ................ 424/177; 260/112.5 R, 260/112.5 E

[56] References Cited

U.S. PATENT DOCUMENTS 4,198,398  4/1980  Hudson et al. ...................... 424/177
4,242,256 12/1980  Sharpe et al. ................ 260/112.5 R Primary Examiner—Delbert R. Phillips
Assistant Examiner—F. T. Moezie
Attorney, Agent, or Firm—Larson and Taylor

[57] ABSTRACT

Preparation of renin inhibitors based on the structure of natural renin substrate at residues 6 to 13 from the amino terminal thereof, the inhibitors being polypeptide analogues having in particular an isosteric non-peptide link corresponding to the 10, 11 peptide link of the substrate, and preparation of dipeptide analogues.

24 Claims, No Drawings

ENZYME INHIBITORS

The invention relates to renin-inhibiting peptide analogues.

BACKGROUND

Renin is a natural enzyme, disorders in relation to which are implicated in many cases of hypertension. It is released into the blood from the kidney, and cleaves from a blood glycoprotein a decapeptide known as angiotensin-I. Circulating angiotensin-I is cleaved in lung, kidney and other tissues to an octapeptide, angiotensin-II, which raises blood pressure both directly by causing arteriolar constriction and indirectly by stimulating release of the sodium-retaining hormone aldosterone from the adrenal gland and thus causing a rise in extracellular fluid volume. The latter effect is caused by angiotensin-II itself or a heptapeptide cleavage product angiotensin-III.

Inhibitors of renin have therefore been sought, with two ends in view, first the provision of a diagnostic agent for identification of cases of hypertension due to renin excess, and secondly the provision of an agent for control of hypertension in such cases.

The present inventors' approach has been to consider the peptide sequence characterising the natural renin substrate at its binding site, and to seek peptide analogues sufficiently similar to bind to the enzyme, in competition with the natural substrate, but sufficiently dissimilar to it to be cleaved slowly or not at all. Such analogues will block the action of the enzyme and attack the hypertension at source.

Renin is specific to a particular bond in the substrate, the N-terminal sequence of which in the horse is for example:

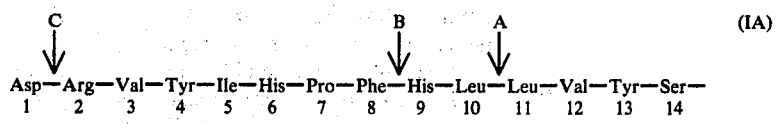

as found by L. T. Skeggs et al J. Exper. Med. 106 439 (1957). Human renin substrate has a different sequence recently discovered by D. A. Tewkesbury et al Biochem. Biophys. Res. Comm. 99 1311 (1981)

the sequence to the left of the arrow A being as in formula (IA).

Cleavage at A gives angiotensin-I; subsequent cleavage at the Phe-His bond at B gives angiotensin-II; and cleavage subsequently again at the Asp-Arg bond at C gives angiotensin-III.

Peptides similar to certain partial sequences of the substrate have been shown to act as inhibitors of renin in vitro. An example is the tetrapeptide ester (the relation to the substrate residues being indicated by numbering):

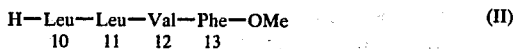

proposed by Kokubu, Nature, 217 456 (1968) but it is inactive in vivo, because of binding to plasma proteins and rapid attack by natural peptidases.

One of the present inventors undertook some years ago a development of Kokubu's work, seeking a renin inhibitor active in vivo, in which analogues of peptides similar to Kokubu's were made but having a methylene imino group —CH$_2$—NH— in place of the peptide link —CO—NH— between the leucine residues. One of these analogues was:

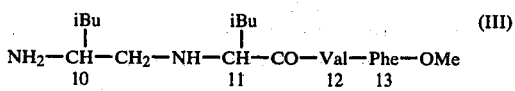

which is the tetrapeptide (I) modified at the Leu-Leu link, leucine of course being

This analogue (III) was the first effective in-vivo inhibitor of renin and was shown to have significant antihypertensive action in Goldblatt hypertensive rats (Parry, Russell and Szelke p. 541 in "Chemistry and Biology of Peptides" Ed. Meienhofer, Ann Arbor Science Publishers 1972). Little or no attention has however been paid to the work, which the authors themselves were unable to pursue, in spite of considerable activity in the general field of substrate-based inhibitors for renin, reviewed for example by Haber & Burton, Federation Proc. 38 No. 13 2768–2773 (1979).

THE INVENTION

The present invention is a development of the above work. Behind it is a concept of modifying peptide structures related to the peptide sequence at the site of action of renin on the natural substrate, by isosteric substitution at, at least, the site of cleavage. Optionally further there is isosteric substitution or other modification at other positions to increase stability or to modify the properties of the final peptide, for example its solubility under physiological conditions or its resistance to in vivo exopeptidase attack. Such modification may for example be by incorporation of residues other than those of the natural L-amino acids; by protection of the N-terminus with acetyl, pivaloyl, t-butyloxycarbonyl (Boc), benzoyl or other groups; or by conversion of the C-terminal carboxyl to another functional group, e.g. the corresponding alcohol, present as such or in ether or ester form.

General reference to amino acids and amino acyl residues and side chains in both the description and claims herein is to be taken as reference to such whether naturally occurring in proteins or not and to both D- and L- forms, and amino is to be taken as including imino except where an aromatic acid, residue or side chain is specified.

The compounds of the present invention, showing desirable renin inhibitory action, are of the general formula:

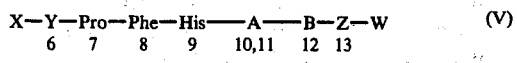

where Pro, Phe and His may be in substituted form;

X=H; or an acyl or other N-protecting group e.g. acetyl, pivaloyl, t-butyloxycarbonyl (Boc), benzoyl or lower alkyl (primarily $C_1$-$C_5$); or an L- or D-amino-acyl residue, which may itself be N-protected similarly;

Y=D- or L-His or other D- or L- basic or aromatic amino-acetyl residue, or is absent;

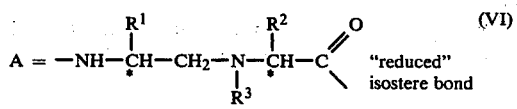

or

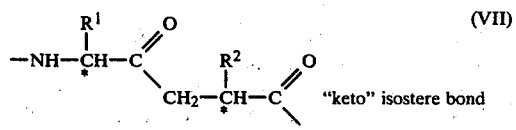

or

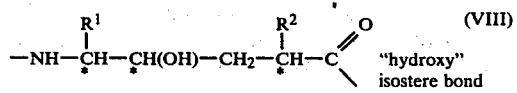

or

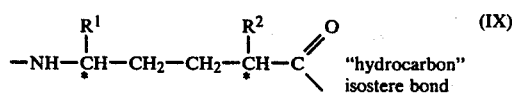

where the configuration at asymmetric centres * is either R or S, where in VIII the hydroxy group may be present as such or protected in ether —$OR^4$ or ester

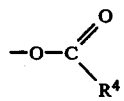

form where $R^4$ is as given under W below and where $R^1$ and $R^2$, the same or different=$^i$Pro (isopropyl), $^i$Bu (isobutyl), Bzl (benzyl) or other lipophilic or aromatic amino-acid side chain $R^3$=—H; lower alkyl ($C_1$-$C_5$); or —$SO_2Ph$, —$SO_2C_6H_4CH_3(p)$, Boc, formyl or other N-protecting group;

B=D- or L- Val or Ile or other D- or L- lipophilic aminoacyl residue;

Z=D- or L- Tyr, Phe, His or other L- or D- aromatic aminoacyl residue; and

W=
(a) —OH (b) —$OR^4$ where $R^4$=(i) lower alkyl $C_1$-$C_5$ (ii) cycloalkyl $C_3$-$C_7$ or Bzl
(c) —$NH_2$
(d) —$NHR^5$ or —$N(R^5)_2$ wherein $R^5$ is an N-protecting group or $R^4$
(e) L- or D-Lys
(f) L- or D-Arg unprotected as the ester or amide
(g) L- or D-Ser and
(h) amino alcohol derived from (e)–(g) as such or protected in ester or ether form Z+W=alcohol derived from
(i) L-Tyr
(ii) L-Phe
(iii) D-Tyr or D-Phe
(iv) His such polypeptide being in the above form or modified by isosteric replacement of one or more remaining peptide bonds by reduced, —$CH_2$—NH—, keto,

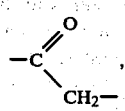

hydroxy, —CH(OH)—$CH_2$—, or hydrocarbon, —$CH_2$—$CH_2$— isosteric links and further being in free form or in protected or salt form at one or more remaining peptide, carboxyl, amino, hydroxy or other reactive groups, in particular as their physiologically acceptable acid addition salts at basic centres.

The above compounds may in particular be those related to the substrate sequence in the horse (B=Val at position 12) or those related to the substrate sequence in man (B=Ile at position 12). Particular groups of these compounds are set out in claims 2 and 3 respectively herein, as formulae VA and VB to which reference may be made but which are not repeated at this point.

The numbering of residues in formulae (V), (VA) and (VB) shows the correspondence with the renin substrates themselves, but without limitation of the generality of the formulae.

Where a peptide bond in addition to that corresponding to the Leu-Leu or Leu-Val bond in the natural renin substrate is isosterically substituted, the 7,8 and 8,9 positions i.e. the Pro-Phe and Phe-His bonds in formula V are preferred, or possibly both of these positions, and it is further preferred that the substitution should be

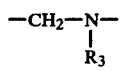

where $R_3$ is as set out above. The alternative isosteric substitutions set out herein may however be used.

Protective or substituent groupings as mentioned above may be any of these known in the polypeptide art, amply disclosed in the literature and not requiring discussion at length here. Generally the selection of the 'protective' groups is according to their function, some being primarily intended to protect against undesired reaction during synthetic procedures while the N- and C-terminal substituents are for example directed against the attack of exopeptidases on the final compounds or to increase their solubility and hence physiological acceptability.

It is in particular possible for one or more remaining peptide bonds in the compounds of formula (V), (VA) or (VB) to be N-substituted with protective groups.

The invention further lies (i) In a diagnostic test for high renin states, blood pressure falling most when renin is high, and as a surgical prognostic test for renovascular hypertension (renal artery stenosis), the administration of a polypeptide analogue as above followed by monitoring of blood pressure, and such polypeptide analogues when for such use, and (ii) In the long and short term treatment of heart failure and all forms of hypertension particularly those associated with high serum renin levels, the administration of a renin-inhibiting amount of a polypeptide analogue as above, and such polypeptide analogues when for such use.

The long and short term response of blood pressure to renin inhibitors is predictive of surgical outcome. In all cases single and repeated doses and any conventional form of pharmaceutical composition may be used, for administration by intranasal or oral route, injection, or any other means as convenient. Amounts may for example be 0.001 to 10 mg/kg body weight daily more usually 0.01 to 1 mg, according to the potency of the analogue and the severity of the condition. Dosage unit compositions may contain such amounts or submultiples thereof to make up the daily dose. (Dosages herein and in the claims are related to the free base content where compounds are in salt form.)

The invention still further extends to a product and method of making a hydroxy or keto isostere of a dipeptide wherein a derivative of a halohydrin preferably a bromohydrin or haloketone preferably a bromoketone $$NH_2CH-CH-CH_2Br \quad \text{or} \quad NH_2CH-C \overset{R^6}{\underset{CH_2-Br}{\diagdown}} \overset{O}{\diagup}$$
$$\phantom{NH_2CH-}\underset{OH}{|}$$

wherein $R^6$ is an amino acid side chain and the $NH_2$ and OH groups are in protected form is subjected to an alkylation procedure to attach a group $$\underset{|}{\overset{R^7}{|}} \\ -CH-COOH$$

and gives the desired isostere as such or in protected form, $R^7$ being the same or a different amino acid side chain.

In particular the alkylation procedure may be
(i) by reaction with an alkali metal carboxylic acid derivative preferably a lithium derivative $$\underset{|}{\overset{R^7}{|}} \\ LiCH-COOLi$$

where $R^7$ is as above.
(ii) by reaction with an alkali metal malonic ester derivative preferably a sodium derivative $$\underset{|}{\overset{COOR^8}{|}} \\ NaCH \\ \underset{|}{COOR^8}$$

where $R^8$ is an esterifying group and a halide preferably an iodide $$R^7\text{-I}$$

where $R^7$ is as above to give intermediate $$NH_2-\overset{R^6}{\underset{|}{CH}}-CH-CH_2-\overset{R^7}{\underset{|}{C}}-COOR^8 \quad \text{or}$$
$$\phantom{NH_2-CH-}\underset{OH}{|} \phantom{CH_2-}\underset{COOR^8}{|}$$

$$NH_2-\overset{R^6}{\underset{|}{CH}}-C\overset{O}{\underset{\diagdown}{\diagup}} \\ \phantom{NH_2-CH-C}CH_2-\overset{R^7}{\underset{|}{C}}-COOR^8 \\ \phantom{NH_2-CH-CCH_2-}\underset{COOR^8}{|}$$

in protected form which intermediate is then decarboxylated and if desired deprotected to give the desired isostere $$NH_2-\overset{R^6}{\underset{|}{CH}}-CH-CH_2-\overset{R^7}{\underset{|}{CH}}-COOH \quad \text{or}$$
$$\phantom{NH_2-CH-}\underset{OH}{|}$$

$$NH_2-\overset{R^6}{\underset{|}{CH}}-C\overset{O}{\underset{\diagdown}{\diagup}} \\ \phantom{NH_2-CH-C}CH_2-\overset{R^7}{\underset{|}{CH}}-COOH$$

as such or in protected form.

The hydroxy isosteres so produced may further be oxidised to the corresponding keto isosteres, and such method and the isosteres produced fall within the invention.

In particular the methods may be applied to the production of a hydroxy dipeptide isostere of the formula $$X^1-NH-\overset{R^1}{\underset{*}{CH}}-CH(OH)-CH_2-\overset{R^2}{\underset{*}{CH}}-C\overset{O}{\underset{\diagdown W^1}{\diagup}}$$

or the corresponding keto isosteres, where the significance of *,
$X^1$ is
(a) lower aliphatic acyl $C_1$-$C_5$ (e.g. formyl, acetyl, pivaloyl)
(b) N-protecting group, e.g. t-butyloxycarbonyl, benzyl-oxycarbonyl, 2,2,2-trichloroethoxycarbonyl or
(c) lower alkyl $C_1$-$C_5$; and
$W^1$ is
(a) —OH or
(b) —$OR^9$ where $R^9$=lower alkyl $C_1$-$C_5$ (e.g. Me, ᵗBu) or =aralkyl (e.g. benzyl).

The dipeptide isosteres given by all these methods may be incorporated in higher peptide analogues by the methods herein described or by the methods of peptide synthesis as generally known in the art, and the invention extends to the dipeptide whether as such or in the form of said higher analogues, in all cases as the compound itself or in protected form.

The dipeptide analogue syntheses are illustrated in detail herein, in the course of illustrating the preparation of the octapeptides and related compounds to which the invention chiefly relates.

Specific analogues within the invention, all as such or in protected form, are

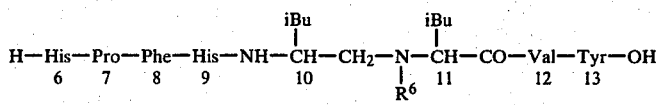

(H-76 where $R^6$ = hydrogen; H-78 where $R^6$ = $SO_2Ph$)

and the corresponding analogue (H-77) with $R^6$=hydrogen and D-His at position 6. A further analogue, with the same methylene-imino isosteric replacement of a Leu-Leu peptide bond is:

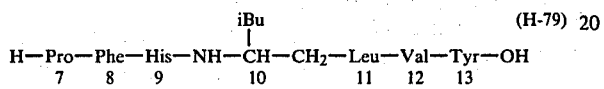

Further analogues within formula (VA) are given in the present disclosure in Examples VI to IX, XI and XII. Analogues within formula (VB) are given in Examples V and X.

SYNTHETIC METHODS

The inventors have developed synthetic methods for the isosteric replacement of the peptide bond —CO—NH— with alternative groups, specifically —CH₂—NH— (reduced), —CH₂CH₂— (hydrocarbon),

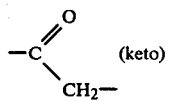

and —CH(OH)—CH₂— (hydroxy) isosteres (see, e.g. Szelke, et al, pp. 57-70 in "Molecular Endocrinology" Vol. 1, Editors: MacIntyre and Szelke, Elsevier, Amsterdam 1977, and Hudson, Sharpe and Szelke, U.S. Pat. No. 4,198,398 "Enkephalin Analogues").

Reference may be made to these publications for general discussion of such isosteric replacement. A reaction sequence for the preparation in particular of the reduced isostere of leucyl leucine for incorporation in the analogues disclosed herein is however for example:

Scheme 1
Synthesis of the protected reduced isostere of L-leucyl-L-leucine

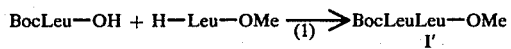

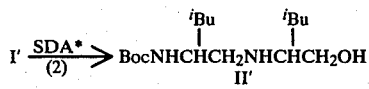

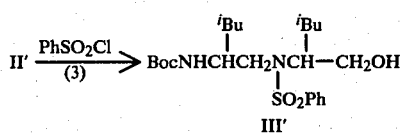

-continued
Scheme 1
Synthesis of the protected reduced isostere of L-leucyl-L-leucine

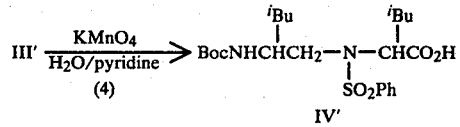

*Sodium di(methoxyethoxy) aluminium hydride (1) Boc-Leucyl-leucine methyl ester

The dipeptide I′ was prepared from Boc-leucine.H₂O (27.5 g, 0.11 mole) and leucine methyl ester.HCl (20 g, 0.11 mole) by mixed anhydride coupling using N-methyl morpholine and isobutylchloroformate. After a standard work-up procedure the dipeptide I′ was obtained as white needles, 35.0 g (88%) from EtOAc/petrol bpt 40°-60°, m.p. 132°-133°

(2) Preparation of compound II′

The dipeptide I′ (7.2 g, 20 mmole) was dissolved in benzene (120 ml, Na-dried). A solution of sodium dihydro-bis(2-methoxyethoxy)aluminate (SDA, 70% in toluene, 41 ml) was added slowly with cooling. After addition, the solution was refluxed for ½ hr, cooled and poured into 0.5 M ice-cold citric acid solution. At pH 2.5 the aqueous solution was extracted with ether (4X) and the combined extracts were discarded. The pH was adjusted to 9 with Na₂CO₃ solution and the aqueous solution was saturated with sodium chloride. Extraction with ether (4X), followed by drying (Na₂SO₄) of the combined organic phases, evaporation and crystallisation from petrol (40°-60°) at −20° gave the reduced dipeptide II′:5.1 g (78%) as white needles.
m.p. 59°-60°.

Nmr (CDCl₃) 9.05-9.15 (12H, d, 4×<u>CH₃</u>) 8.75 (6H, m, 2×(CH₃)₂<u>CH-CH₂</u>); 8.55 (9H, s, (<u>CH₃</u>)₃CO); 7.35 (5H,m, <u>CH₂NH</u>, <u>CH₂OH</u>); 6.05-6.85 (3H,m, 2×α-<u>CH</u> and <u>CH₂OH</u>); 5.3 (1H, d, Boc <u>NH</u>—).

(3) Protection of compound II′ with benzenesulphonyl

The reduced compound II′ (11.0 g, 34.7 mmole) in dioxan (100 ml) was added to a solution of KHCO₃ (21 g., 6 equiv.) in H₂O (100 ml). This mixture was cooled in ice and benzene-sulphonyl chloride (9.0 ml, 2 equiv.) added in dioxan (25 ml) with vigorous stirring. Stirred at 22° overnight. Poured into ether, washed with 2 N NH₄OH (4X), H₂O (1X) 0.5 M citric acid (2X to remove any unsulphonated material), H₂O (1X).

The protected compound III′ was obtained as an oil. Nmr spectroscopy showed the presence of one benzenesulphonyl group. This material was used without further purification in the next stage:

(4) Oxidation of compound III′

The material from the preceding preparation was taken up in pyridine (50 ml), cooled in ice and KMnO₄ (11.0 g 70 mmole) in H₂O (50 ml) and pyridine (100 ml)

added. Stirred for 42 hrs at 20°. The MnO₂ precipitate was removed and the filtrate diluted with citric acid solution until acidic. Ether extraction at pH 5 removed product and starting material. The product IV' was obtained by (i) NaHCO₃ extraction-to remove strongly acidic by-products (ii) extracted with 30% v/v 0.880 ammonia solution (6X). The ammonia washes contained essentially pure IV'. Starting material remaining in the ether was re-oxidised for 42 hrs and worked-up as above.

The total amount of IV' (isolated by acidifying the ammonia washes and extracting with CHCl₃) obtained was 2.34 g (20% based on II').

The material was a colourless foam Rf 0.41 by TLC on silica in benzene-dioxan-acetic acid (95:25:4).

Nmr (CDCl₃): 8.9–9.3 (12H, m, 4×C$\underline{H}$₃); 8.2–8.8 (15H, m, (C$\underline{H}$₃)₃CO and 2×(CH₃)₂C$\underline{H}$—C$\underline{H}$₂); 5.4–7.0 (4H, m, 2×α—C$\underline{H}$ and —C$\underline{H}$₂—N—); 2.0 and 2.4 (5H,m, C₆$\underline{H}$₅SO₂), 1.2 (1H,br.s, CO₂$\underline{H}$).

Alternatively, the reduced Leu-Leu analogue IV may be synthesised by the following method:

SCHEME 2

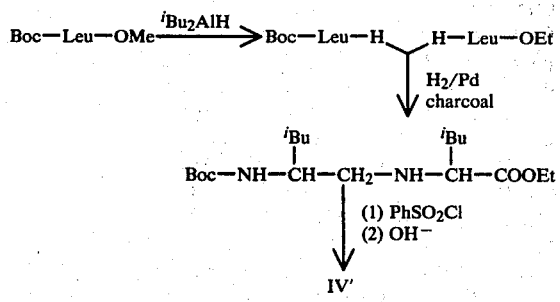

The following is a synthetic method for a reduced Leu-Val isostere by a preferred route.

(1) Boc-L-Leucinal, 1

Boc-L-Leucine methyl ester (22.7 g, 90 mmoles) in dry toluene (250 ml) under N₂ was cooled to −78° and 25% di-isobutylaluminium hydride in toluene (130 ml, 225 mmoles) were added over 25 mins. keeping the temperature under −70°. The mixture was stirred for 15 mins. at −78° after completion of the addition, then MeOH (10 ml) was added cautiously. When effervescence ceased the mixture was poured into an ice-cold solution of Rochelle salt (100 ml of saturated solution + 600 ml H₂O). This mixture was shaken until an extractable solution was obtained. The toluene was separated and the aqueous phase re-extracted with ether (2 × 300 ml). Toluene and ether extracts were combined and dried (Na₂SO₄). The resulting oil was passed rapidly through a pad of silica gel in 15% EtOAc/petrol 40°-60°. The crude aldehyde was obtained as an oil, weight 18.68 g. Nmr showed aldehyde content to be 85%, therefore yield of aldehyde: 15.9 g (83%).

Nmr (CDCl₃), τ: 0.45 (1H,s,C$\underline{H}$O); 4.87 (H,br.d.,Boc N$\underline{H}$): 5.83 (1H,br.m., NH—C$\underline{H}$CHO); 8.43-8.93 (12H,m,(C$\underline{H}$₃)₃C, (CH₃)₂C$\underline{H}$.C$\underline{H}$₂); 9.0 and 9.1 (12H, 2×d, (C$\underline{H}$₃)₂CH) TLC: (solvent 30% EtOAc/petrol 60°-80°), Rf=0.43.

(2) Boc-L-Leucyl-L-valine benzyl ester reduced isostere, 2

L-Valine-OBzl (10 mmoles, from EtOAc/1 N NaHCO₃ partition of 3.8 g of p-toluene sulphonate salt) and Boc-L-Leucinal (2.54 g, 10 mmole aldehyde content) in dry tetrahydrofuran (20 ml) stood over 5 Å molecular sieve (10 g) overnight. Sodium cyanoborohydride (630 mg, 10 mmoles) in MeOH (3 ml) was added with cooling, then left at room temperature for 30 mins. The mixture was diluted with methylene chloride (100 ml), filtered and evaporated to dryness. The residue was passed down a silica column in 20% EtOAc/petrol Scheme 3
Synthesis of the Protected Reduced Isostere of L-Leucyl-L-Valine

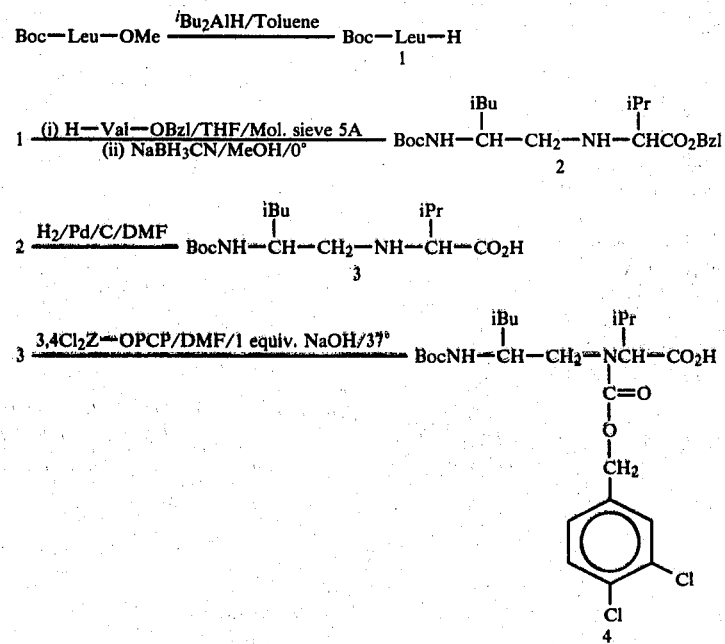

(60°-80°) to remove polar impurities. Isostere containing factions were combined. Crystallisation from petrol 60°-80° at −20° gave large clusters of needles, 1.52 g (38%).

τ: 2.65(5H,s,OCH$_2$C$_6$H$_5$); 6.35(1H,m,NHCHCO$_2$Bzl); 7.05 (1H,m,NH—CHCH$_2$); 7.45(2H,m, —CH$_2$NH—); 8.25-8.90(13H,m, (CH$_3$)$_3$CO—.) (CH$_3$)$_2$ CHCH$_2$ and (CH$_3$)$_2$CH—); 9.05 and 9.15 (12H, 2×s, 2×(CH$_3$)$_2$CH).

TLC: (Solvent: 30% EtOAc/petrol 60°/80°) Rf=0.39.

(3) N-(2S)-t-Butyloxycarbonylamino-4-methylpentyl, N-(3,4-dichlorobenzyloxycarbonyl)-L-valine, 4

Boc-L-Leucyl-L-valine, benzyl ester-reduced-isostere (1.5 g 3.68 mmoles) in dimethylformamide (60 ml) was hydrogenated at STP over 5% Pd/C (150 mg). After 3½ hrs. the colloidal solution was flushed with nitrogen and 1 M NaOH (3.8 ml, 1.05 equiv.) was added followed by 3,4-dichlorobenzyl pentachlorophenyl carbonate (1.92 g, 4.07 mmoles). The mixture was kept at 50° in a stoppered flask for 24 hrs. and then evaporated to dryness. EtOAc was added and the Pd/C filtered off. The EtOAc solution was washed with 1 M citric acid (2 x), H$_2$O (1 x), brine (1 x), and dried (Na$_2$SO$_4$).

The ctrude isostere 4 was chromatographed on silicagel (Merck Keiselgel 60, 40–63 m) eluting with 2% MeOH/CHCl$_3$ to give the title compound as a colourless oil.

Nmr(CDCl$_3$), τ: 2.5–2.9(3H,m,C$_6$Cl$_2$H$_3$); 3.3–3.8 (2H,br,BocNH and CO$_2$H); 4.85 and 4.95 (2H,2×s, OCH$_2$—C$_6$Cl$_2$H$_3$); 5.5–6.3(2H,m,NHCHCH$_2$ and —NCHCO$_2$H); 6.5–7.2 (2H br, 2×d, CHCH$_2$N—); 8.2–8.9 (13H,m,(CH$_3$)$_3$CO, (CH$_3$)$_2$CHCH$_2$ and (CH$_3$)$_2$CH—); 8.9–9.4 (12H,m,2×(CH$_3$)$_2$CH).

TLC: (solvent 5% MeOH/CHCl$_3$) Rf=0.32.

EXAMPLES

The following detailed Examples illustrate the invention.

The Examples are preceded by the preparation of Boc-Tyr [Bzl (2, 6 Cl$_2$)]-O-resin. (Reaction times marked * are convenient rather than necessary.) Preparation of Resin Boc-Tyr [Bzl(2,6 Cl$_2$)]-OH (1.65 g, 3.75 mmol) was dissolved in ethanol (20 ml) and water (5 ml) added. The pH was brought to 7.0 with cesium bicarbonate solution and the solvent evaporated in vacuo. The residue was treated twice with toluene and evaporated to remove the last traces of water leaving a white powder which was dried for several hours over phosphorus pentoxide. The residue was dissolved in DMF (65 ml), chloromethylated resin (10 g, 7.5 mequiv.) added and the reaction stirred at 37° for four days.

The resin was then filtered and washed thoroughly with DMF, DMF/water (9:1) and then DMF again. The resin was then resuspended in DMF (65 ml) and treated with acetic anhydride (2.36 ml, 25 mmol) and triethylamine (3.5 ml, 25 mmol) for 3 days.

The resin was filtered, washed thoroughly with DMF, DMF/water (9:1) and methanol and dried. The resin was then "defined" by shaking a suspension in dichloromethane and removing the particles slowest to float. The resin was then dried.

Yield 10.8 g.

Amino-acid analysis: (12 N-HCl/propionic acid 1:1 130°, 2 hours) gave an incorporation of 0.11 mmol/g.

EXAMPLE I

H-His-Pro-Phe-His-Leu-reduced-Lev-Val-Tyr-OH
(H-76)

Boc-Tyr[Bzl(2,6 Cl$_2$)]-O-Resin (3 g, 0.6 mmol) was washed with reagents in the following sequence: CH$_2$Cl$_2$ (3X) iPrOH (2X), CH$_2$Cl$_2$ (3X), 40% TFA/CH$_2$Cl$_2$ 1 min then 20 min, CH$_2$Cl$_2$ (3X), iprOH (2X), CH$_2$Cl$_2$ (3X), 40% TFA/CH$_2$Cl$_2$ 1 min then 20 min, CH$_2$Cl$_2$ (3X) iPrOH (2X) CH$_2$Cl$_2$ (3X), 10% Et$_3$N/CH$_2$Cl$_2$ (2×2 min), CH$_2$Cl$_2$ (5 X). Boc-Val-OH (0.65 g, 3 mmol) was then coupled using DCCI (0.68 g, 3.3 mmol) and HOBt (0.92 g, 6 mmol) in DMF/CH$_2$Cl$_2$ (1:1) for 17 hours.* The resin was then washed with DMF (3X), CH$_2$Cl$_2$ (3X), iPrOH (2X), CH$_2$Cl$_2$ (3X) 10% Et$_3$N/CH$_2$Cl$_2$ (2 min), CH$_2$Cl$_2$ (5X then acetylated using acetylimidazole (0.66 g, 6 mmol) in DMF for 1 hour. The resin was then washed with DMF (3X) CH$_2$Cl$_2$ (3X) iPrOH (2X) and finally CH$_2$Cl$_2$ (3X).

This sequence of washes and reactions was repeated for the addition of each of the residues with the following modifications.

After deprotection of the Boc-Val-Tyr [Bzl (2,6 Cl$_2$)]-O-resin Boc-NH-CH(CH$_2$CHMe$_2$)-CH$_2$-N(SO$_2$Ph)-CH(CH$_2$CHMe$_2$)-CO$_2$H (0.42 g, 0.9 mmol) was coupled using DCCI (0.28 g, 1.35 mmol) and HOBt (0.275 g, 1.8 mmol) in DMF/CH$_2$Cl$_2$(1:1) for 18 hours, followed by acetylation using acetylimidazole (0.66 g, 6 mmol) in DMF for 1 hour.

After deprotection, Boc-His(Dnp)-OH (1.44 g, 3 mmol) was coupled using DCCI (0.68 g, 3.3 mmol) and HOBt (0.92 g, 6 mmol) for 2 hours, followed by acetylation for 1 hour.

Deprotection of the histidyl peptide was achieved using 50% TFA/CH$_2$Cl$_2$ instead of the usual 40% TFA/CH$_2$Cl$_2$. Boc-Phe-OH (0.796 g, 3 mmol) was coupled using DCCI (0.68 g, 3.3 mmol) and HOBt (0.92 g, 6 mmol) for 17½ hours*, followed by acetylation for 1 hour.

Deprotection of the phenylalanyl peptide was achieved using the usual 40% TFA/CH$_2$Cl$_2$. Boc-Pro-OH (0.646 g, 3 mmol) was coupled using DCCI (0.68 g, 3.3 mmol) and HOBt (0.92, 6 mmol) for 2 hours followed by acetylation for 1 hour.

After deprotection Boc-His(Dnp)-OH (1.44 g, 3 mmol) was coupled using DCCI (0.68 g, 3.3 mmol) and HOBt (0.92 g, 6 mmol) for 14½ hours* followed by acetylation for 1 hour.

The resin was then washed with DMF (3X), CH$_2$Cl$_2$(3X) prOH (2X), CH$_2$Cl$_2$(3X) and finally MeOH (3X) and dried to give 3.5353 g of product.

1.2 g of this material was treated with HF at 0° for 1¼ hours in the presence of anisol (1.5 ml) then dried overnight over potassium hydroxide. The resin was then washed with DMF/water (101), acetic acid and finally acetic acid/water (1:1) to remove the peptide. These washes were combined and evaporated in vacuo.

The residue was dissolved in DMF (15 ml) and water (6 ml) thioethanol (5 ml) added and the pH of the solution brought to 8.0 with sodium carbonate. The reaction was stirred overnight the solvent evaporated and the residue applied to a Sephadex G 25 column (72×2.5 cms) eluted with 50% acetic acid at 18 mls/hr collecting 6 ml fractions. Fractions 27–46 were combined and the solvent evaporated in vacuo and dried. Then 90% of the residue was taken (for the rest see Example III) and dissolved in anhydrous ammonia (100 ml) and small portions of sodium wire added until a permanent blue colour was achieved for 15 seconds. The ammonia was allowed to evaporate and the residue dried.

The residue was applied to a Sephadex SPC25 column (77×1.6 cms) eluted with 30% acetic acid at 40 mls/hr, with a sodium chloride gradient from 0.01 M to 1 M over two days collecting 6.6 ml fractions.

The product was contained in fractions 100–104. These were pooled, evaporated and the residue dissolved in glacial acetic acid and filtered to remove the sodium chloride. The solution was evaporated and desalted on a Sephadex G25 column (72×2.5 cms) eluted with 50% acetic acid at 18 mls/hr collecting 6 ml fractions. Fractions 32–6 were pooled, evaporated, transferred to a vial and lyophilised.

| Yield 13.4 mg | | | | |
|---|---|---|---|---|
| Product | $C_{52}H_{74}O_9N_{12}$ | MW. 1011,25 | | |
| T.l.c. | Rf 0.15 | EtOAc/Pyr/AcOH/H$_2$O | 40:20:6:11 | |
| (silica) | Rf 0.40 | nBuOH/Pry/AcOH/H$_2$O | 30:20:6:24 | |
| T.l.e. | pH 2.1 | 1000V | 30 min | mobility 8.3 cm. |
| | pH 6.5 | 1000V | 30 min | mobility 7.5 cm. |
| AAA | 6N HCl + phenol 110°, 40 hours, peptide content 72% | | | |
| His: 1.97; Pro: 1.01; Val: 1.02; Tyr: 0.98; Phe: 1.01. | | | | |

EXAMPLE II

H-Pro-Phe-His-Leu-reduced-Leu-Val-Tyr-OH (H-79)

Fractions 80–84 of the SPC 25 Sephadex column from the previous synthesis were combined, evaporated and the residue dissolved in glacial acetic acid and filtered to remove sodium chloride. The solution was evaporated and the product desalted on a Sephadex G25 column (72×2.5 cms) eluted with 50% acetic acid at 18 mls/hr collecting 6 ml fractions. Fractions 32–9 were pooled, evaporated, transferred to a vial and lyophilised.

| Yield 23.6 mg | | | | |
|---|---|---|---|---|
| Product | $C_{46}H_{67}O_8N_9$ | MW 874,10 | | |
| Tlc | Rf 0.29 | EtOAc/Pyr/AcOH/H$_2$O | 40:20:6:11 | |
| (silica) | Rf 0.46 | nBuOH/Pyr/AcOH/H$_2$O | 30:20:6:24 | |
| Tle | pH 2.1 | 1000V | 30 min mobility | 7.5 cms |
| | pH 6.5 | 1000V | 30 min mobility | 8.3 cms |
| AAA | 6N HCl + phenol, 110°, 40 hours, peptide content 85% | | | |
| His: 0.97; Pro: 1.08; Val: 0.99; Tyr: 0.97; Phe: 1.00. | | | | |

The above example illustrates how Y in formulae (V), (VA) and (VB) may be absent.

EXAMPLE III

H-His-Pro-Phe-His-Leu-reduced (SO$_2$Ph)-Leu-Val-Tyr-OH (H-78)

In the synthesis of compound H76 10% of the residue from the Sphadex G25 column after the HF and thioethanol treatments of the resin was kept.

This material was applied to a Sephadex SPC25 column (77×1.6 cm) eluted with 30% acetic acid at 20 mls/hr with a sodium chloride gradient from 0.01 M to 1 M over 2 days collecting 6.6 ml fractions.

The product was contained in fractions 74–7. These were pooled, evaporated, dissolved in glacial acetic acid and filtered to remove sodium chloride. The solution was then evaporated and desalted on a Sephadex G25 column (72×2.5 cms) eluted with 50% acetic acid at 18 mls/hr collecting 6 ml fractions. Fractions 31–4 were pooled evaporated, the residue transferred to a vial and lyophilised.

| Yield 0.6 mg | | | | |
|---|---|---|---|---|
| Product | $C_{58}H_{78}O_{11}N_{12}S$ | MW: 1151.40 | | |
| Tlc | Rf 0.31 | EtOAc/Pyr/AcOH/H$_2$O | 40:20:6:11 | |
| (silica) | | | | |
| Tle | pH 2.1 | 1000v | 30 min mobility | 5.4 cms. |
| AAA | 6N HCl + phenol, 40 hrs, 110°, peptide content 64% | | | |
| His: 1.93; Pro: 1.08; Val: 1.05; Tyr: 0.96; Phe: 0.97. | | | | |

EXAMPLE IV

H-DHis-Pro-Phe-His-Leu-reduced-Leu-Val-Tyr-OH,

The Boc-Tyr [Bzl(2,6,Cl$_2$)]-O-Resin (3 g, 0.6 mmol) was deprotected and Boc-Val-OH (0.65 g, 3.0 mmol) was coupled using DCCI (0.68 g, 3.3 mmol) and HOBt (0.92 g, 6 mmol) for 22 hours* then acetylated with acetylimidazole (0.66 g, 6 mmol) for 1 hour.

After deprotection, Boc-Leu-reduced (SO$_2$Ph)-Leu-OH, IV, (0.42 g 0.9 mmol) was coupled using DCCI (0.28 g, 1.35 mmol) and HOBt (0.275 g, 1.8 mmol) for 20 hours, then acetylated for 1 hour.

After deprotection Boc-His(Dnp)-OH (1.44 g, 3 mmol) was coupled using DCCI (0.68 g, 3.3 mmol) and HOBt (0.92 g, 6 mmol) for 22 hours*, then acetylated for 1 hour.

After deprotection, this time with 50% TFA/CH$_2$Cl$_2$ Boc-Phe-OH (0.796 g, 3 mmol) was coupled with DCCI (0.68 g, 3.3 mmol) and HOBt (0.92 g, 6 mmol) for 19 hours* then acetylated for 1 hour.

After deprotection Boc-Pro-OH (0.646 g, 3 mmol) was coupled using DCCI (0.68 g, 3.3 mmol) and HOBt (0.92 g, 6 mmol) for 3 hours then acetylated for 1 hour.

The peptide was again deprotected and coupled with Boc-D-His(Boc)-OH (0.91 g, 2.56 mmol using DCCI (0.58 g, 2.82 mmol) and HOBt (0.78 g, 5.1 mmol) for 2 hours, then acetylated for 1 hour.

The resin was washed with DMF (3X) CH$_2$Cl$_2$ (3X) iProH (2X) CH$_2$Cl$_2$ (3X and finally MeOH (3X) and dried to give 3.6563 g of product.

1.2 g of this material was treated with HF at 0° for 1¼ hours in the presence of anisole (1.5 ml) then dried overnight over potassium hydroxide. The resin was then washed with DMF, DMF/H$_2$O (1:1), acetic acid and finally acetic acid/water (1:1) to remove the peptide. These washes were combined and evaporated in vacuo.

The residue was dissolved in DMF (15 ml) and water (6 ml), thioethanol (5 ml) added and the pH of the solution brought to 8.0 with sodium carbonate solution. The reacton was stirred overnight the solvent evaporated and the residue applied to a Sephadex G 25 column (72×2.5 cms) eluted with 50% acetic acid at 18 mls/hr collecting 6 ml fractions. Fractions 27–46 were combined and the solvent evaporated in vacuo and dried.

90% of the residue was dissolved in anhydrous ammonia (100 ml) and small portions of sodium wire added until a permanent blue colour was achieved for 15 seconds. The ammonia was allowed to evaporate and the residue dried.

The residue was applied to a Sephadex SPC 25 column (77×1.6 cms) eluted with 30% acetic acid at 20 mls/hr with a sodium chloride gradient 0.01 M to 1 M over 2 days collecting 6.6 ml fractions.

The product was contained in fractions 88–92. These were pooled and the residue dissolved in glacial acetic acid and filtered to remove the sodium chloride. The solution was evaporated and desalted on a Sephadex G 25 column (72×2.5 cms) eluted with 50% acetic acid at 18 mls/hr collecting 6 ml fractions. Fractions 32–41 were pooled, evaporated, transferred to a vial and lyophilised.

| Yield 46.8 mg | | | | |
|---|---|---|---|---|
| Difference in yields between "L-His" and "D-His" compounds was accounted for by a lower incorporation of the isostere in the "L" case and less removal of the histidine with Na/NH$_3$. | | | | |
| Product | C$_{52}$H$_{74}$O$_9$N$_{12}$ | MW 1011,25 | | |
| Tlc (silica) | Rf 0.18 | EtOAc/Pyr/AcOH/H$_2$O | 40:20:6:11 | |
| Tle | pH 2.1 1000V | 30 min | mobility | 7.7 cm |
|  | pH 6.5 1000V | 30 min | mobility | 7.9 cm |
| AAA | 6N—HCl + phenol, 110°, 40 hours; peptide content 93% | | | |
| His: 1.98; Pro: 1.00; Val: 1.08; Tyr: 0.97; Phe 0.97 | | | | |

EXAMPLE V

H-His-Pro-Phe-His-Leu-reduced-Val-Ile-His-OH (H 113)

The method is generally that of Example I above but illustrates formula (VB).

Preparation of Boc-His (DNP)-O-Resin (AH/30/83)

Boc-His(DNP)-OH. (4.74 g, 11.25 mmol) was dissolved in ethanol (60 ml) and a solution of cesium bicarbonate (2.18 g, 11.25 mmol) in water (15 ml) added. The solvent was evaporated in vacuo and the residue treated four times with toluene and evaporated to remove water before finally drying overnight over phosphorus pentoxide. The residue was dissolved in DMF (175 ml), chloromethylated resin (30 g, 22.5 m-equiv.) added and the reaction stirred at 37° for five days.

The resin was filtered off and washed thoroughly with DMF, DMF/water (9:1) and then DMF again. It was resuspended in DMF (175 ml) and treated with acetic anhydride (7.08 ml, 75 mmol) and triethylamine (10.5 ml, 75 mmol) overnight.

The resin ester was filtered, washed thoroughly with DMF, DMF/water (9:1) and methanol and dried. It was then "de-fined" by shaking it in dichloromethane and removing the particles in the supernatant. Finally, the resin was dried. Yield: 30.45 g. A trial coupling with Boc-Ala-OH, followed by amino-acid analysis (after hydrolysis with 12 n-HCl/propionic acid 1:1, 130°, 2hrs) gave an incorporation of 0.22 mmol/.

Coupling to Resin Ester

Boc-His(DNP)-O-Resin (2.5 g 0.55 mmol) was deprotected with 50% TFA/CH$_2$Cl$_2$ and Boc-Ile-OH (0.748 g 3 mmol) was coupled using DCCI (0.68 g, 3.3 mmol) and HOBt (0.92 g, 6.0 mmol) for 2 hours, then acetylated with acetyl imidazole (0.55 g, 5 mmol) overnight*.

After deprotection with 40% TFA/CH$_2$Cl$_2$, Boc-Leu-reduced (3,4-Cl$_2$-Z)-Val-OH, 4 (0.343 g, 0.66 mmol) was coupled using DCCI (0.15 g, 0.73 mmol) and HOBt (0.202 g, 1.32 mmol) for 16 hours, then acetylated for 1 hour.

After deprotection, Boc-His(DNP)-OH (1.26 g, 3.0 mmol) was coupled using DCCI (0.68 g, 3.3 mmol) and HOBt (0.92 g, 6 mmol) for 2 hours, then acetylated for 1 hour.

After deprotection, again with 50% TFA/CH$_2$Cl$_2$, Boc-Phe-OH (0.796 g, 3 mmol) was coupled with DCCI (0.68 g, 3.3 mmol) and HOBt (0.92 g, 6 mmol) for 3 hours* then acetylated overnight*

After deprotection, Boc-Pro-OH (0.646 g, 3 mmol) was coupled using DCCI (0.68 g, 3.3 mmol) and HOBt (0.92 g, 6 mmol) for 2 hours then acetylated for 1 hour.

The peptide was again deprotected and coupled with Boc-His(DNP)-OH (1.26 g, 3 mmol) using DCCI (0.68 g, 3.3 mmol) and HOBt (0.92 g, 6 mmol) for 2 hours, then acetylated overnight*.

The peptide resin ester was washed with DMF (3X), CH$_2$Cl$_2$ (3X) iProH (2X), CH$_2$Cl$_2$ (3X) and finally MeOH (3X) and dried. It was then treated with HF at 0° for 1¼ hours in the presence of anisole (4 ml) and dried overnight over potassium hydroxide. The resin was washed with DMF, acetic acid and acetic acid/water (1:1) to remove the peptide. The washes were combined and evaporated in vacuo.

The residue was dissolved in DMF(60 ml) and water (24 ml), thioethanol (10 ml) was added and the pH of the solution brought to 8.0 with sodium carbonate solution. The reaction mixture was stirred overnight, the solvent evaporated and the residue applied to a Sephadex G25 column (77×2.5 cms). It was eluted with 50% acetic acid at 18 mls/hr collecting 6 ml fractions. Fractions 34–53 were combined and the solvent evaporated in vacuo and dried.

| Product | C$_{49}$H$_{72}$O$_3$N$_{14}$ | MW 985,21 |
|---|---|---|
| Tlc (silica) | Rf = 0.63 in EtOAc—Py—AcOH—H$_2$O (15:20:6:11) | |

AA analysis in accordance with calculated composition.

EXAMPLES VI–IX

These Examples illustrate formula (VA). The methods disclosed above are applied to condensing Boc-Phe-H or Boc-Leu-H with H-Phe-OBzl, reducing the imine link, deprotecting at the carboxyl terminus and protecting the nitrogen of the reduced peptide link to give:

$$\text{Boc—NH—CH(R)—CH}_2\text{—N(ZCl}_2\text{)—CH(Bzl)—CO}_2\text{H}$$

12 R = Bzl
12a R = iBu
ZCl$_2$ = 3,4-dichloro benzyloxy carbonyl

This Phe-reduced-Phe or Leu-reduced-Phe analogue is then used as follows:

| VI | Use of 12 (Phe—reduced-Phe) in an analogue otherwise as H-77 (see Example IV) |
|---|---|
| VII | Use of 12a (Leu—reduced-Phe) in an analogue otherwise as H-77 (see Example IV) |
| VIII | Use of 12 in an analogue as H-76 (Example I), viz: |

(H 110)
H—His—Pro—Phe—His—Phe—reduced-Phe—Val—Tyr—OH
  6    7    8    9   10           11   12   13

IX    Use of 12a in an analogue as H-76 (Example I), viz:

(H 115)
H—His—Pro—Phe—His—Leu—reduced-Phe—Val—Tyr—OH
  6    7    8    9   10           11   12   13

EXAMPLE X

This Example illustrates formula (VB), the method of Example V being used but the Tyr resin of Examples I to IV, to give:

EXAMPLE XIII

The reaction scheme below, also suitable for other hydroxy dipeptide analogues, was used to synthesise an N-terminal and hydroxy-group protected Leu-Leu hydroxy isostere 18.

Scheme 4

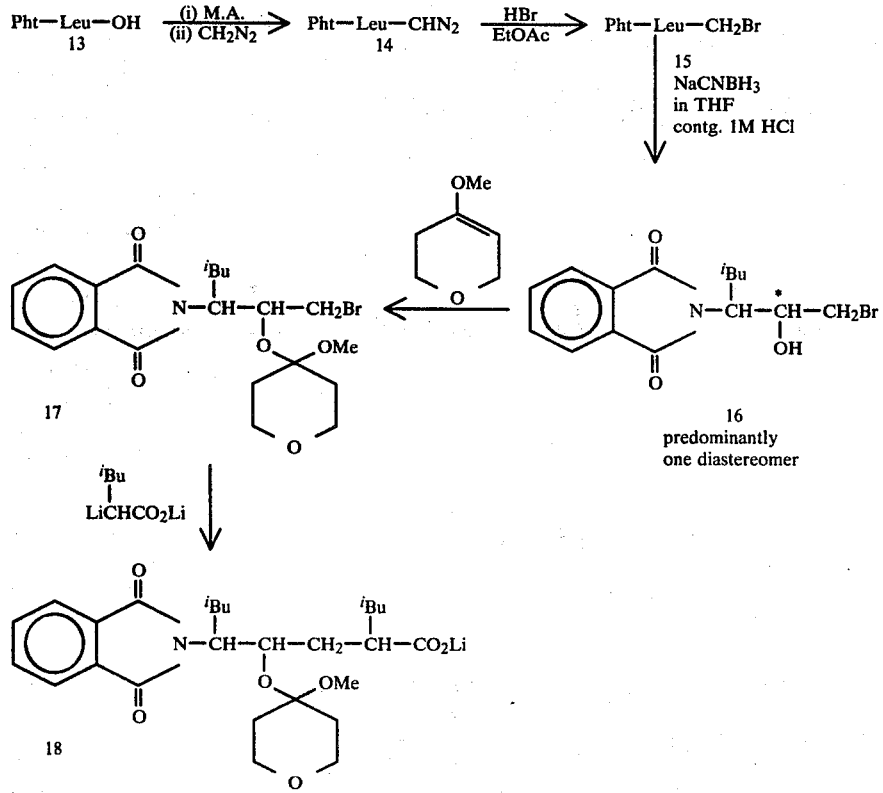

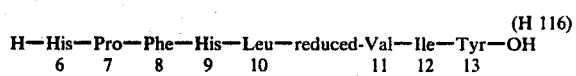

(H 116)

EXAMPLE XI

Using of the methods disclosed herein to give:

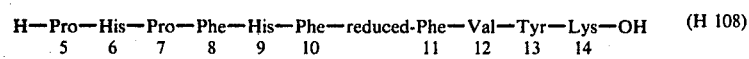

(H 108)

this being an analogue illustrating the non-crticality of the terminal portions of the chain allowing X and W in formulae (V), (VA) and (VB) to represent further residues. It is a further example of formula (VA).

EXAMPLE XII

Use of the methods disclosed herein to give:

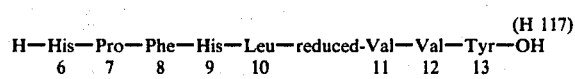

(H 117)

a compound of value in its relation to the Leu-Val structure at 11, 12 in human renin substrate.

The following Example illustrates the synthesis of hydroxy and keto isoesteres.

M.A. = isobutyl chloroformate/triethylamine; Pht = phthaloyl.

The resulting N-terminal phthaloyl protected, —OH protected hydroxy isostere of Leu-Leu can be coupled direct for example to valyl tyrosine, followed by removal of the phthaloyl group, coupling direct to a suitable tri or tetrapeptide, and deprotection at the —OH group by mild acid hydrolysis, to give for example analogues corresponding to H-76 (Example 1), H-79 (Example 2), H-77 (Example 4). Alternatively the phthaloyl group may be removed by treatment with hydrazine and a new protective group, e.g. benzyloxycarbonyl or t-butyloxycarbonyl attached prior to coupling. The methods used after the preparation of the protected hydroxy isostere are those of the peptide synthesis art, well known in themselves and exemplified in detail herein. The compounds specifically prepared are:

(a) H-His-Pro-Phe-His-Leu-hydroxy-Leu-Val-Tyr-OH
(b) H-Pro-Phe-His-Leu-hydroxy-Leu-Val-Tyr-OH
(c) H-DHis-Pro-Phe-His-Leu-hydroxy-Leu-Val-Tyr-OH

EXAMPLE XIV

The alternative and preferred reaction scheme below, also suitable for other dipeptide hydroxy isosteres was used to synthesise an N-terminal and hydroxy-group protected Leu-Val hydroxy isostere 23.

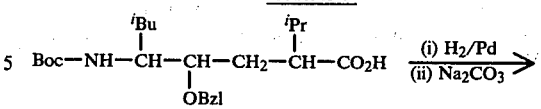

Scheme 6

Scheme 5
Pht = Phthaloyl, Thp = Tetrahydropyranyl

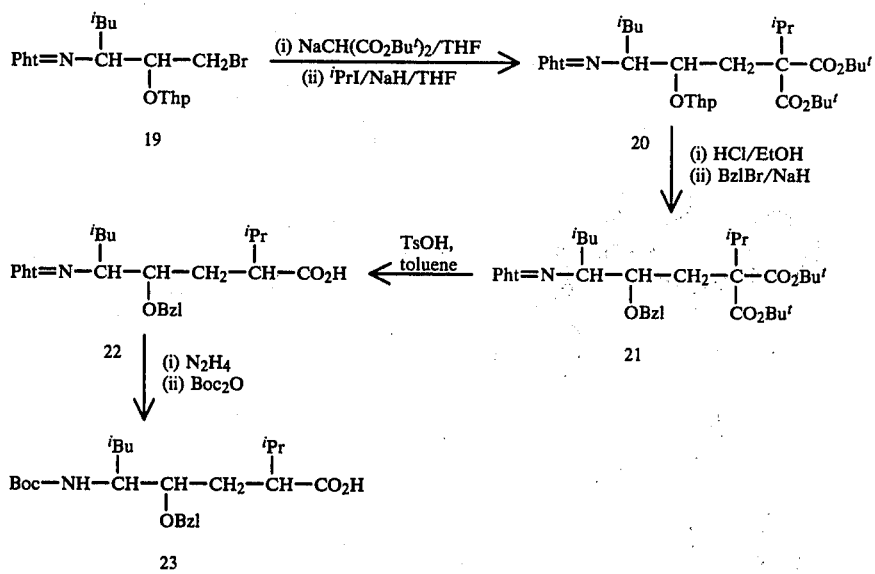

In the above scheme the protected bromohydrin 19 is obtained in the same way as the corresponding intermediate 17 in Scheme 4, and is subjected to malonic ester synthesis and alkylation with isopropyl iodide to give the malonic ester derivative 20. Protection on the hydroxyl function is changed from Thp to Bzl to yield 21 and the latter is subjected to protonolysis and decarboxylation. In the resulting isostere acid 22 amino protection is changed from Pht to Boc yielding the protected isostere 23 which is suitable for incorporation into an octapeptide analogue by the usual methods of solid phase peptide synthesis to give for example the octapeptide analogue:

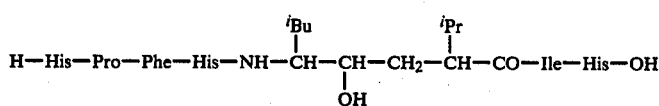

This is a Leu-hydroxy-Val isostere.

EXAMPLE XV

Keto isosteres may be produced for example by the method of published U.K. Specification No. 1,587,809 (U.S. 4,242,256) of R. Sharpe and one of the present inventors M. Szelke, to which reference may be made. Alternatively they may be prepared from hydroxy isosteres prepared as disclosed herein and in particular, in the present Example, from the final product 21 of scheme 5 as in the scheme below:

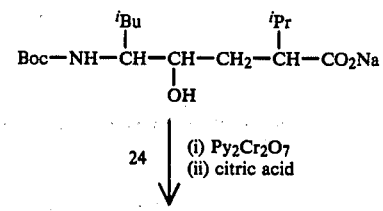

In the above scheme the benzyl protection is selectively removed from the hydroxyl function of 23 and the free acid is is converted into its sodium salt 24. The latter is subjected to oxidation by pyridinium dichromate and acidification to give the partially protected keto isostere acid which is ready for incorporation into an octapeptide analogue by the usual methods of solid phase synthesis, for example the analogue:

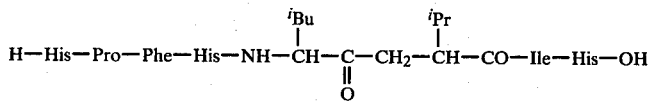

This is a Leu-keto-Val isostere.

Alternatively the keto isostere may be prepared directly by a modified version of scheme 5 wherein the bromohydrin 19 is replaced by the bromoketone 15 (scheme 4), which is:

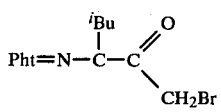

giving the compound

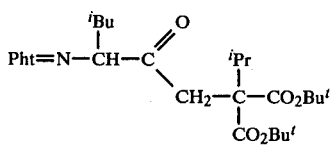

which is successively treated with TsOH, toluene and (i) N₂H₄, (ii) Boc₂O to give:

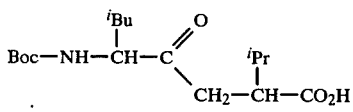

The following examples are of the methods of diagnosis and treatment according to the invention.

EXAMPLE XVI

A person suffering from hypertension is given repeated doses of a nasal instillation preparation of 0.01 to 1 mg/kg body weight of the compound H 108 (Example 9), per dose, three times a day. Clinically significant maintained reduction of the hypertension is a positive indication of hypertension amenable to treatment by the method of the invention.

Comparable amounts of the compounds of other Examples such as Examples 1, 3, 4, 5, 8, 9 and 10 may be substituted and the method may be similarly applied to patients in heart failure, as referred to herein. In both the hypertension and the heart failure instances the plasma-renin may or may not be above normal.

EXAMPLE XVII

A person diagnosed as suffering from amenable hypertension by the method of Example 16 is treated by means of a continuing course of the compound H 108 (Example 9) or other compound as exemplified herein, in the amounts set out in Example 16.

ACTIVITY IN VITRO

Preliminary activity test results in the human renin-renin substrate reaction in vitro are given in the table below, with comparative figures for the tetrapeptide analogue (III). The test is based on the methods described by J. A. Millar et al. in Clinica Chimica Acta (1980) 101 5-15 and K. Poulsen and J. Jorgensen in J. Clin. Endocrinol. Metab. (1974) 39 816.

It is based on the measurement, by radioimmunoassay, of Angiotensin-I released from human renin substrate by human renin in human plasma. The inhibitor is dissolved in 0.01 N HCl (10 μl) and added to human plasma (75 μl) containing EDTA, and angiotensin-I antibody (15 μl) in 3 M-Tris/HCl buffer (pH 6.9).

After incubation at 37° C. for 0-120 mins., the enzymic reaction is quenched by the addition of ice-cold 0.25 M Tris/HCl buffer (pH 7.4) containing 0.01% of bovine serum albumin. 125I-labelled angiotensin-I is added, followed by equilibration at 4° C. for 48 hours. Free and bound ligand are separated by the addition of dextran-coated charcoal, and the amount of bound radio-ligand determined in a gamma counter.

The results for the renin inhibitory activities of the present compounds thus tested, expressed as the IC$_{50}$ (the molar concentration required to cause 50% inhibition), are as follows:

| Analogue | | IC$_{50}$ | |
| --- | --- | --- | --- |
| Example I | (H-76) | 1.0 μM | |
| Example II | (H-79) | 17.0 μM | |
| Example III | (H-78) | 1.5 μM | |
| Example IV | (H-77) | 1.0 μM | |
| Example V | (H-113) | 0.26 μM | ** |
| Example VI | | | * |
| Example VII | | | * |
| Example VIII | (H-110) | 1.3 μM | |
| Example IX | (H-115) | 2.5 μM | |
| Example X | (H-116) | 0.20 μM | |
| Example XI | (H-108) | 0.05 μM | |
| Example XII | (H-117) | | * |
| Example XIII | (a) | | * |
| | (b) | | * |
| | (c) | | * |
| Example XIV | | | * |
| Example XV (Comparative) III | | 822 μM | |

*Preliminary indication of comparable activities.
**The corresponding non-isosteric peptide has for example been tested and shows a potency over three orders of magnitude less (IC$_{50}$ 400 μM)

These are most notable results, showing a potency, in the reduction of renin activity remaining in the plasma in the presence of the analogue, several orders of magnitude greater than the previously proposed tetrapeptide analogue.

ACTIVITY IN VIVO

The activity tests below are in animals but indicate corresponding activity in man.

In in vitro studies, in plasma from both normal and sodium-depleted dogs, the compound H-77 (Example IV) inhibited renin. In in vivo studies H-77 was infused into normal conscious sodium-depleted dogs at rates of 0.01, 0.1, 1 and 10 mg/kg/hr. A maximum fall in blood pressure, plasma renin (PR) angiotensin-I (A-I) and angiotensin-II (A-II) levels was obtained within 10 minutes at doses of 1 and 10 mg/kg/hr. When the infusion was stopped, blood pressure returned to baseline levels 30 minutes after the 1 mg/kg/hr. dose, but more slowly after the 10 mg/kg/hr. dose.

In the claims below it will be understood that compounds may be in the form shown or in protected or salt form at NH$_2$, COOH, OH or other active groups and in particular as their physiologically acceptable acid addition salts at basic centres. Further as already noted herein general reference to amino acids and amino acyl residues and side chains is to be taken as reference to such whether naturally occurring in proteins or not and to both D- and L- forms, and amino is to be taken as including imino except where an aromatic acid, residue or side chain is specified.

We claim:

1. A polypeptide analogue of the formula:

$$Z-Y-Pro-Phe-His-A-B-Z-W \quad (V)$$
$$\phantom{Z-Y-}6\phantom{-}7\phantom{-Pro-}8\phantom{-Phe-}9\phantom{-}10,11\phantom{-}12\phantom{-}13$$

where: Pro, Phe and His may be in substituted form;
X=H, a lower aliphatic acyl (C$_1$–C$_5$), t-butyloxycarbonyl, an aromatic acyl or an L- or D- aminoacyl residue, which may itself be N-protected similarly;
Y=D- or L-His or other D- or L- basic or aromatic aminoacyl residue, or is absent;

$$A = -NH-\overset{R^1}{\underset{*}{C}H}-CH_2-\underset{R^3}{N}-\overset{R^2}{\underset{*}{C}H}-C\overset{O}{\diagdown} \quad \text{"reduced" isostere bond} \quad (VI)$$

or $$NH-\overset{R^1}{\underset{*}{C}H}-C\overset{O}{\diagdown}{CH_2-\overset{R^2}{\underset{*}{C}H}-C\overset{O}{\diagdown}} \quad \text{"keto" isostere bond} \quad (VII)$$

or $$-NH-\overset{R^1}{\underset{*}{C}H}-\underset{*}{CH(OH)}-CH_2-\overset{R^2}{\underset{*}{C}H}-C\overset{O}{\diagdown} \quad \text{"hydroxy" isostere bond} \quad (VIII)$$

or $$-NH-\overset{R^1}{\underset{*}{C}H}-CH_2-CH_2-\overset{R^2}{\underset{*}{C}H}-C\overset{O}{\diagdown} \quad \text{"hydrocarbon" isostere bond} \quad (XI)$$

where the configuration at asymmetric centres * is either R or S, where in VIII the hydroxy group may be present as such or protected in either —OR$^4$ or ester $$-O-C\overset{O}{\underset{R^4}{\diagdown}}$$

form where R$^4$ is as given under W below and where R$^1$ and R$^2$, the same or different=$^i$Pro (isopropyl),
$^i$Bu (isobutyl), Bzl (benzyl) or other lipophilic or aromatic amino-acid side chain;
R$^3$=—H; lower alkyl (C$_1$–C$_5$); or —SO$_2$Ph, —SO$_2$C$_6$H$_4$CH$_3$(p), Boc, formyl or other N-protecting group;

B=D- or L- Val or Ile or other D- or L- lipophilic aminoacyl residue;
Z=D- or L- Tyr, Phe, His or other L- or D-aromatic amino-acyl residue; and
W=
 (a) OH
 (b) —OR$^4$ where R$^4$=(i) lower alkyl C$_1$–C$_5$ (ii) cycloalkyl C$_3$–C$_7$ or Bzl
 (c) —NH$_2$
 (d) —NHR$^5$ or —N(R$^5$)$_2$ wherein R$^5$ is an N-protecting group or R$^4$
 (e) L- or D-Lys
 (f) L- or D-Arg unprotected or as the ester or amide
 (g) L- or D-Ser and
 (h) amino alcohol derived from (e)-(g) unprotected protected as such or in ester or ether form;
Z+W=alcohol derived from
 (i) L-Tyr
 (ii) L-Phe
 (iii) D-Tyr or D-Phe
 (iv) His such polypeptide being in the above form or modified by isosteric replacement of one or more remaining peptide bonds by reduced, —CH$_2$—NH—, keto, $$-C\overset{O}{\underset{CH_2-}{\diagdown}},$$

hydroxy, —CH(OH)—CH$_2$—, or hydrocarbon, —CH$_2$—CH$_2$— isosteric links and further being in free form or in protected form at one or more remaining peptide, carboxyl, amino, hydroxy or other reactive groups.

2. A polypeptide analogue, according to claim 1, of the formula:

$$X-Y-Pro-Phe-His-A-Val-Z-W \quad (VA)$$
$$\phantom{X-Y-}6\phantom{-}7\phantom{-Pro-}8\phantom{-Phe-}9\phantom{-}10,11\phantom{-}12\phantom{-}13$$

where
X, Y, Pro, Phe and His are as in claim 1
A is as in claim 1 except that
 R$^1$ and R$^2$, the same or difference=$^i$Bu (isobutyl) or Bzl (benzyl) or other lipophilic or aromatic amino-acid side chain;
 R$^3$=—H; or —SO$_2$Ph, —SO$_2$C$_6$H$_4$CH$_3$(p), Boc, formyl or other N-protecting group;
Z=Tyr, Phe or his other;
W=
 (a) —OH
 (b) —OR$^4$ where R$^4$=(i) lower alkyl C$_1$–C$_5$ (ii) cycloalkyl C$_3$–C$_7$ or Bzl
 (c) —NH$_2$
 (d) —NHR$^5$ or —N(R$^5$)$_2$ wherein R$^5$ is an N-protecting group or R$^4$
 (f) L- or D-Lys
 (g) L- or D-Arg unprotected or as the ester or amide
 (h) L- or D-Ser and
 (j) amino alcohol derived from (f)-(h) unprotected or protected as such or in ester or ether form;
Z+W=alcohol derived from
 (i) L-Tyr
 (ii) L-Phe
 (iii) D-Tyr or D-Phe (iv) His.

3. A polypeptide analogue, according to claim 1, of the formula:

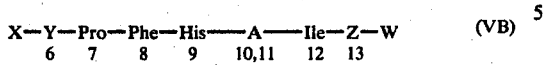

where
X, Y, Pro, Phe and His are as in claim 1
A is as in claim 1 except that
  $R^1 = {}^i$Bu (isobutyl) or Bzl (benzyl) or other lipophilic or aromatic amino-acid side chain
  $R^2 = {}^i$Pr (isopropyl), and
  $R^3 =$ —H; or —$SO_2$Ph, —$SO_2C_6H_4CH_3$(p), Boc, formyl or other N-protecting group
Z is as in claim 1
W is as in claim 2 or
Z+W = an alcohol derived from the aromatic residues specified for Z in claim 1, as such or protected in ester or ether form as specified therein.

4. A polypeptide according to claim 1, modified by isosteric replacement, as set out therein, at one or both of the Pro-Phe or Phe-His links.

5. A polypeptide according to claim 1 wherein the isosteric replacement at at least the 10,11 position is of the "reduced" kind.

6. A polypeptide according to claim 1 wherein the isosteric replacement at at least the 10,11 position is of the "hydroxy" kind.

7. The compound:
H-His-Pro-Phe-His-Leu-reduced-Leu-Val-Tyr-OH.

8. The compound:
H-Pro-Phe-His-Leu-reduced-Leu-Val-Tyr-OH.

9. The compound:
H-His-Pro-Phe-His-Leu-reduced ($SO_2$Ph)-Leu-Val-Tyr-OH.

10. The compound:
H-DHis-Pro-Phe-His-Leu-reduced-Leu-Val-Tyr-OH.

11. The compound:
H-His-Pro-Phe-His-Leu-reduced-Val-Ile-His-OH.

12. The compound:
H-DHis-Pro-Phe-His-Phe-reduced-Phe-Val-Tyr-OH.

13. The compound:
H-DHis-Pro-Phe-His-Leu-reduced-Phe-Val-Tyr-OH.

14. The compound:
H-His-Pro-Phe-His-Phe-reduced-Phe-Val-Tyr-OH.

15. The compound:
H-His-Pro-Phe-His-Leu-reduced-Phe-Val-Tyr-OH.

16. The compound:
H-His-Pro-Phe-His-Leu-reduced-Val-Ile-Tyr-OH.

17. The compound:
H-Pro-His-Pro-Phe-His-Phe-reduced-Phe-Val-Tyr-Lys-OH.

18. The compound:
H-His-Pro-Phe-His-Leu-reduced-Val-Val-Tyr-OH.

19. The compound:
H-His-Pro-Phe-His-Leu-hydroxy-Leu-Val-Tyr-OH.

20. The compound:
H-Pro-Phe-His-Leu-hydroxy-Leu-Val-Tyr-OH.

21. The compound:
H-DHis-Pro-Phe-His-Leu-hydroxy-Leu-Val-Tyr-OH.

22. The compound:
H-His-Pro-Phe-His-Leu-hydroxy-Val-Ile-His-OH.

23. The compound:
H-His-Pro-Phe-His-Leu-keto-Val-Ile-His-OH.

24. A pharmaceutical composition comprising the polypeptide analogue of claim 1 with a pharmaceutically acceptable diluent, said polypeptide analogue being present in a renin-inhibiting amount.

* * * * *

UNITED STATES PATENT AND TRADEMARK OFFICE
CERTIFICATE OF CORRECTION

PATENT NO. : 4,424,207
DATED : Jan. 3, 1984
INVENTOR(S) : Szelke et al

It is certified that error appears in the above-identified patent and that said Letters Patent are hereby corrected as shown below:

Column 23, line 12, in formula (V), change "Z" to --X--;
Column 23, line 17, change "$(C_1=C_5)$" to --$(C_1-C_5)$--;
Column 24, line 17, delete "protected as such";
Column 24, line 46, change "difference" to --different--;
Column 24, line 51, change "his other" to --His--;
Column 24, line 64, delete "protected as such or".
In the title page of the patent under the filing date insert:
    --Foreign Application Priority Date
Aug. 6, 1980  United Kingdom  80 25579
June 12, 1981 United Kingdom  81 18194--

Signed and Sealed this

Ninth Day of October 1984

[SEAL]

Attest:

Attesting Officer

GERALD J. MOSSINGHOFF

Commissioner of Patents and Trademarks